(12) United States Patent
Cipolletti et al.

(10) Patent No.: US 9,855,147 B2
(45) Date of Patent: Jan. 2, 2018

(54) MODULAR PROSTHESIS

(75) Inventors: George B. Cipolletti, Duxbury, MA (US); Carl A. Knobloch, Duxbury, MA (US); Edward J. Cheal, East Taunton, MA (US); Bryan Horan, Franklin, MA (US)

(73) Assignee: OMNI Life Science Inc., Raynham, MA (US)

( * ) Notice: Subject to any disclaimer, the term of this patent is extended or adjusted under 35 U.S.C. 154(b) by 0 days.

(21) Appl. No.: 13/397,083

(22) Filed: Feb. 15, 2012

(65) Prior Publication Data

US 2012/0209391 A1 Aug. 16, 2012

Related U.S. Application Data

(60) Provisional application No. 61/442,988, filed on Feb. 15, 2011.

(51) Int. Cl.
*A61F 2/38* (2006.01)
*A61F 2/30* (2006.01)

(52) U.S. Cl.
CPC .......... *A61F 2/389* (2013.01); *A61F 2/30734* (2013.01); *A61F 2002/30377* (2013.01); *A61F 2002/30383* (2013.01); *A61F 2002/30401* (2013.01); *A61F 2002/30433* (2013.01); *A61F 2002/30507* (2013.01); *A61F 2002/30604* (2013.01); *A61F 2002/30736* (2013.01); *A61F 2002/30828* (2013.01)

(58) Field of Classification Search
CPC ........ A61F 2/30734; A61F 2002/30736; A61F 2220/0025; A61F 2/389

USPC ............................................. 623/20.16, 20.34
See application file for complete search history.

(56) References Cited

U.S. PATENT DOCUMENTS

| | | | |
|---|---|---|---|
| 5,047,058 A | * | 9/1991 | Roberts ............... A61F 2/30734 623/20.16 |
| 5,192,327 A | | 3/1993 | Brantigan |
| 5,194,066 A | * | 3/1993 | Van Zile .................... 623/20.15 |
| 5,387,241 A | * | 2/1995 | Hayes ................. A61F 2/30734 623/20.16 |
| 5,702,464 A | | 12/1997 | Lackey et al. |
| 5,824,103 A | * | 10/1998 | Williams ................... 623/20.32 |
| 5,916,269 A | * | 6/1999 | Serbousek et al. ........ 623/22.24 |
| 6,214,052 B1 | | 4/2001 | Burkinshaw |
| 6,709,461 B2 | * | 3/2004 | O'Neil et al. ............. 623/20.33 |
| 7,175,665 B2 | | 2/2007 | German et al. |

(Continued)

FOREIGN PATENT DOCUMENTS

| | | |
|---|---|---|
| SU | 1607798 A1 | 11/1990 |
| WO | 03061522 A2 | 7/2003 |
| WO | 2006127848 A2 | 11/2006 |

OTHER PUBLICATIONS

International Search Report and Written Opinion for PCT/US2012/025208, dated May 4, 2012.

(Continued)

*Primary Examiner* — Bruce E Snow
*Assistant Examiner* — Melissa Hoban
(74) *Attorney, Agent, or Firm* — Kim Winston LLP

(57) ABSTRACT

Modular prosthesis components having first and second relief patterns, the first relief pattern being complementary to the second relief pattern such that a component having the first relief pattern may seat fully on and in register with a component having the second relief pattern.

22 Claims, 15 Drawing Sheets

(56) References Cited

U.S. PATENT DOCUMENTS

| | | | |
|---|---|---|---|
| 7,753,960 B2 | 7/2010 | Cipolletti et al. | |
| 8,100,977 B2* | 1/2012 | Felt | 623/17.16 |
| 8,100,982 B2 | 1/2012 | Heck et al. | |
| 8,764,760 B2* | 7/2014 | Metzger et al. | 606/88 |
| 8,900,316 B2* | 12/2014 | Lenz et al. | 623/20.32 |
| 2004/0247641 A1* | 12/2004 | Felt et al. | 424/423 |
| 2005/0055097 A1 | 3/2005 | Grunberg et al. | |
| 2006/0015184 A1 | 1/2006 | Winterbottom et al. | |
| 2007/0179627 A1* | 8/2007 | Gustilo et al. | 623/20.15 |
| 2008/0051908 A1 | 2/2008 | Angibaud et al. | |
| 2008/0119939 A1* | 5/2008 | Termanini | 623/20.27 |
| 2008/0133020 A1* | 6/2008 | Blackwell et al. | 623/20.34 |
| 2010/0114323 A1 | 5/2010 | Deruntz et al. | |

OTHER PUBLICATIONS

European Search Report dated Dec. 14, 2016 under Application No. EP 12747299.1.

Australian Examination Report dated Jul. 20, 2015 under Application No. 2012217694.

\* cited by examiner

MODULAR PROSTHESIS

CROSS-REFERENCE TO RELATED APPLICATION

This application claims the benefit of U.S. provisional application Ser. No. 61/442,988, filed Feb. 15, 2011, which is hereby incorporated herein by reference.

FIELD

The present disclosure relates generally to an implantable article that is particularly suitable for use as an artificial joint prosthesis and more particularly to a prosthesis having in part a tray that is supported by metaphyseal bone, such as the tibial component of a knee prosthesis.

BACKGROUND

Artificial joint prostheses are widely used today, restoring mobility to patients affected by a variety of conditions, particularly arthritis. The satisfactory performance of these devices can be affected not only by the design of the component itself, but also by the final placement and geometry of the implanted component, and the long-term fixation of the device. Improper placement or positioning of the device, an improper fit to the patient's anatomy, or an inadequate reconstruction of the bony anatomy can adversely affect the goal of satisfactorily restoring the clinical bio-mechanics and function of the joint.

Joint arthroplasty sometimes requires reconstruction of the patient's bony anatomy due to pre-existing anatomical defects and bone loss. This bone loss may be due to injury, previous reconstructive surgery, or other preexisting conditions. Successful joint arthroplasty, for example, in the knee, sometimes requires restoration of the bone anatomy through the use of implant devices that substitute for significant portions of the bones in the joint, for example, the proximal tibia. Due to the large variation in potential conditions that may be encountered during surgical reconstruction, one approach has been to design a joint replacement system with modular components that augment the surface replacement components to restore the natural alignment and limb length, while also providing the mechanical strength and stability needed for joint function.

SUMMARY

The modular components described herein allow for intraoperative customization of the device to best meet the needs of the patient bone anatomy. A joint prosthesis is built up using modular components (also called "augment blocks"). This modular approach allows for many different potential configurations with a limited number of component part sizes. In this way one can accommodate a wide range of anatomical deficiencies and recreate the normal biomechanics for a well-functioning joint reconstruction.

One disadvantage of previous modular implant designs is the potential risk of material debris generation during service due to relative motion at the interfaces between components. The systems and methods disclosed here alleviate this problem by incorporating interlocking features between mating components in combination with a bolt for compressing and retaining the modular augment block or blocks. The horizontal flat surfaces of the mating blocks and base plate are located so as to insure direct contact at the interlocking features. This direct contact, and the static compressive force provided by the locking bolt, eliminates any spatial clearance or gaps between the mating components, creating a tight fit and minimizing the potential for relative motion between the components.

The modular augments are further improved by the incorporation of mirrored (anti-symmetric) features at the opposite horizontal surfaces. These anti-symmetric features allow the augment blocks to be stacked, with interdigitation of the locking features of adjacent (stacked) blocks, creating a solid and stable construct. The interdigitating features are compatible for all augment sizes which allows the mixing of different sizes of augment block when creating a stack. The sequential stacking of different sizes allows the creation of tapered geometries. For example, in the knee, such a tapered geometry allows use of both an appropriately sized tibial base plate for the mating femoral component, while at the same time providing a bone-facing augment that is appropriate for the supporting tibial bone. As more bone is lost or removed from the proximal tibia, the cross-sectional size of the tibia generally gets smaller than the size at the proximal metaphysis. By stacking augments of various sizes according to the present systems and methods, a practitioner may create a final construct that meets both the dissimilar sizing needs of the knee articulation and that of the remaining tibial bone.

A modular stem may be used with the same tibial tray. The loss of bone that is typical with revision knee surgery can require additional mechanical elements to adequately stabilize the tibial tray. A stem extension from the tibial tray is often used to engage the tibial diaphysis and thus provide mechanical support. This stem is typically attached or integral to the central area of the tibial tray, and is commonly straight, but may also be curved.

The modular stem portion may feature an external taper at its proximal end. The external taper serves as an attachment surface for optional augment blocks to substitute for missing or poor quality bone in the central portion of the recipient's proximal tibia.

It sometimes occurs during knee reconstructive surgery that the geometric center of the remaining proximal tibia is not in line with the geometric center of the tibial plateau. As a consequence, use of a straight tibial stem, centrally fixed in the tibial diaphysis, would result in the tibial tray being in a horizontally displaced location relative to the anatomical center of the knee joint. In some knee replacement systems this problem is solved by providing an "offset" tibial stem, either one piece or modular, that allows a horizontal offset of the long axis of the stem relative to the center of the tibial tray. These offset stems can be problematic in use due to the need to prepare the bone, typically by reaming or drilling, on an axis that is offset from the center of the tibial tray. Use of the present systems and methods avoids the need for additional bone preparation through the use of asymmetrically-sized augment blocks between the medial and lateral undersides of the tibial tray. With one or more larger augment blocks on one side and one or more smaller augment blocks on the other side, the geometric center of the distal end of the augment blocks is horizontally offset from the geometric center of the tibial tray.

Decoupling the tibial tray, stem, and augment block portions results in multiple distinct pieces and thereby offers further benefits. The modular tibial tray portion may be combined with the modular stem portion to allow sizing of the tibial tray portion independent from the stem portion. The modular tibial tray portion may also be combined with one or more modular augment block portions to allow sizing of the distal bone interface independent of the tibial tray portion. By varying tibial tray, stem, and augment block configurations a variety of clinical needs and situations can be addressed such as revision of knee that had undergone previous joint reconstruction without requiring a whole new tibial tray system. Many more clinical situations can be addressed by simply combining the appropriate stems and/or augment block portions with the tibial tray that is appropriate for the knee joint and the mating femoral component.

DETAILED DESCRIPTION

While the present disclosure exemplifies systems and methods in the context of the tibial component of a knee replacement prosthesis for cemented application, the systems and methods have numerous other applications. Examples include cementless tibial knee prostheses and other implantable prostheses such as ankles, fingers, and elbows, each of which may include a tray portion for resurfacing one or both sides of a joint. The present systems and methods are particularly advantageous in allowing optimal sizing and placement for use in an artificial knee and as such this description will reference a knee prosthesis.

Figure 1:
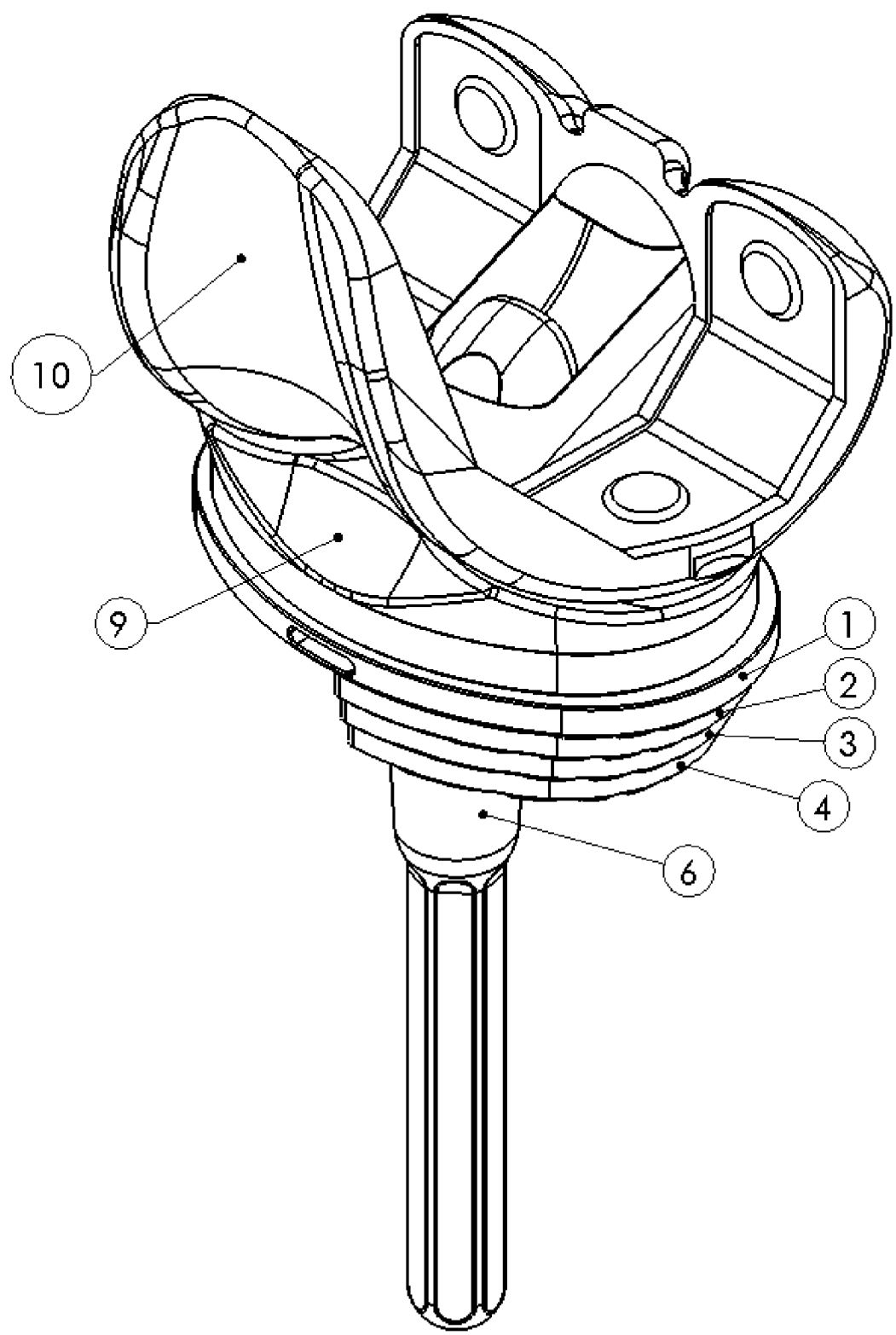
FIG. 1 is an anterior-proximal view of a knee replacement prosthesis including one embodiment of the assembled prosthetic device (tibial tray component).
Figure 2:
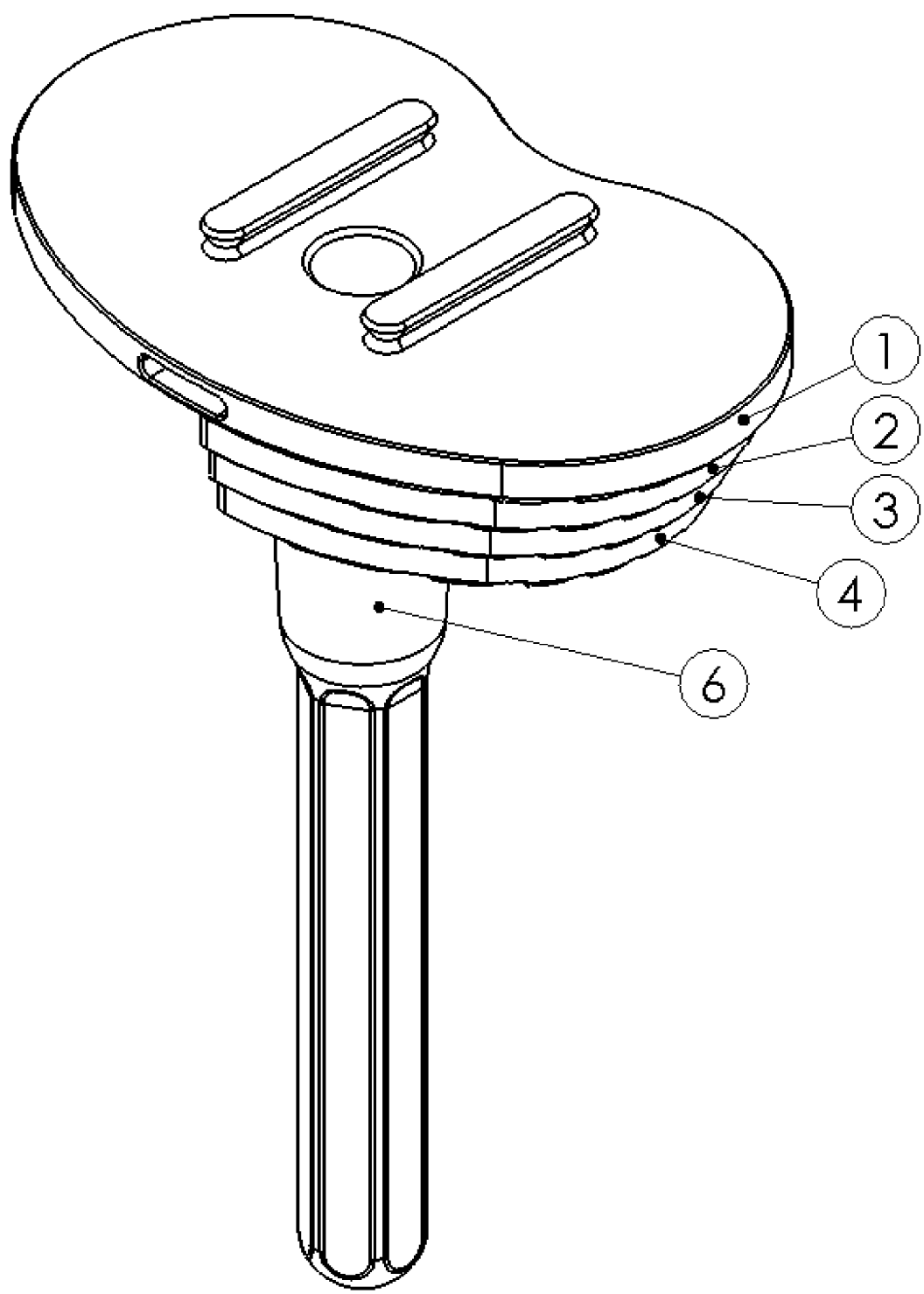
FIG. 2 is a proximal-anterior view of one embodiment of the assembled prosthetic device.
Figure 4:
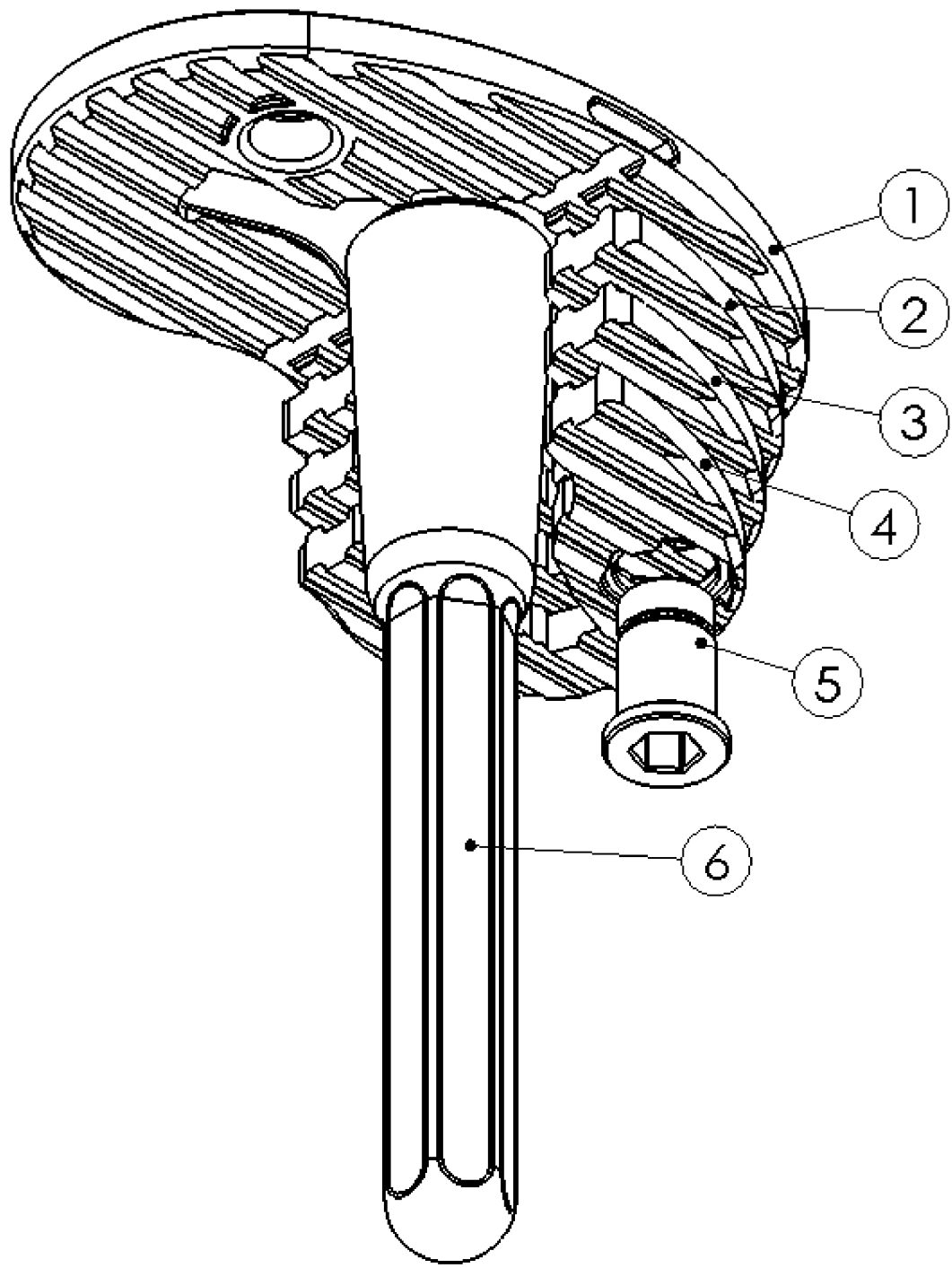
FIG. 4 is an exploded distal view of one embodiment of the prosthetic device.

FIG. 1 shows an embodiment of a modular tibial knee prosthesis. A tray portion (1) of the device interfaces to the proximal end of the tibia. The tibial articular portion (9) fixedly attaches to the tray portion (1), with the aid of some attachment structure (such as the illustrated cleats) on the proximal surface of the tibial tray portion (FIG. 2), together forming the tibial bearing portion. The tray portion (1) is independent from the augment block portions (2-4, 7), the tray and augment block portions being assembled and joined by the attachment mechanism shown in FIG. 4. The tibial articular portion (9) articulates with the femoral portion (10) to complete a functional knee replacement. Optionally, the knee replacement may include a patellar portion (not shown), for resurfacing or replacing the patella, that articulates with the femoral portion.

The tibial tray portion (1) is independent of the tibial articular portion (9), the tibial augment block portions (2-4), and the stem portion (6). The augment block portions (2-4, 7) are attached to the tray portion (1) with an augment locking bolt portion (5). The complete tibial tray assembly may include from zero to many augment blocks on one or both (medial and lateral) sides of the tibial tray portion. Augment locking bolts (5) are in various lengths, each length to accommodate a specific thickness augment block and/or a specific total augment stack thickness. The most augment blocks on a single side would generally be about six, but there is no reason more that more than six augment blocks could not be stacked, provided an appropriate length augment locking bolt is included in the system.

Figure 3:
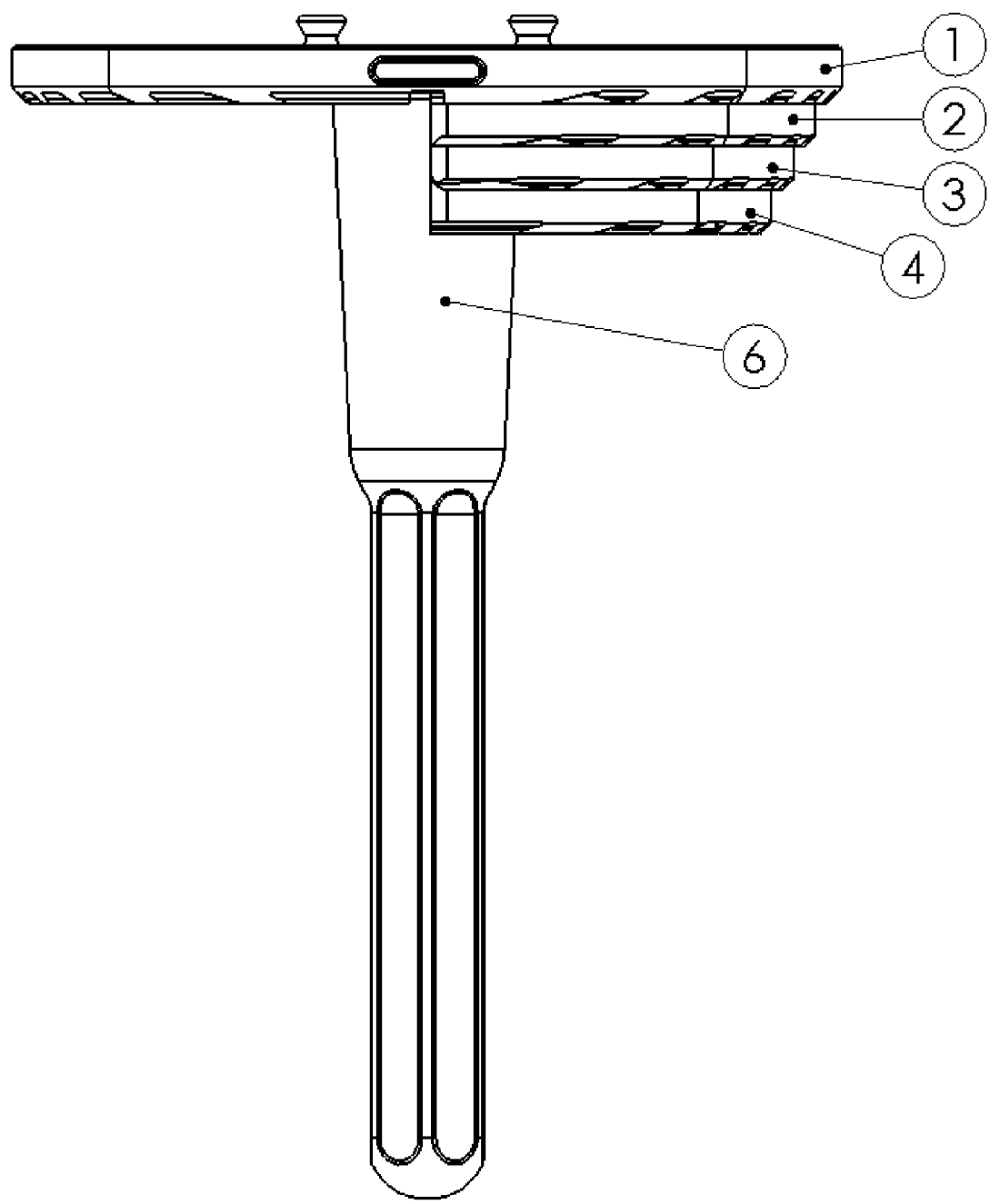
FIG. 3 is an anterior view of one embodiment of the assembled prosthetic device.
Figure 6:
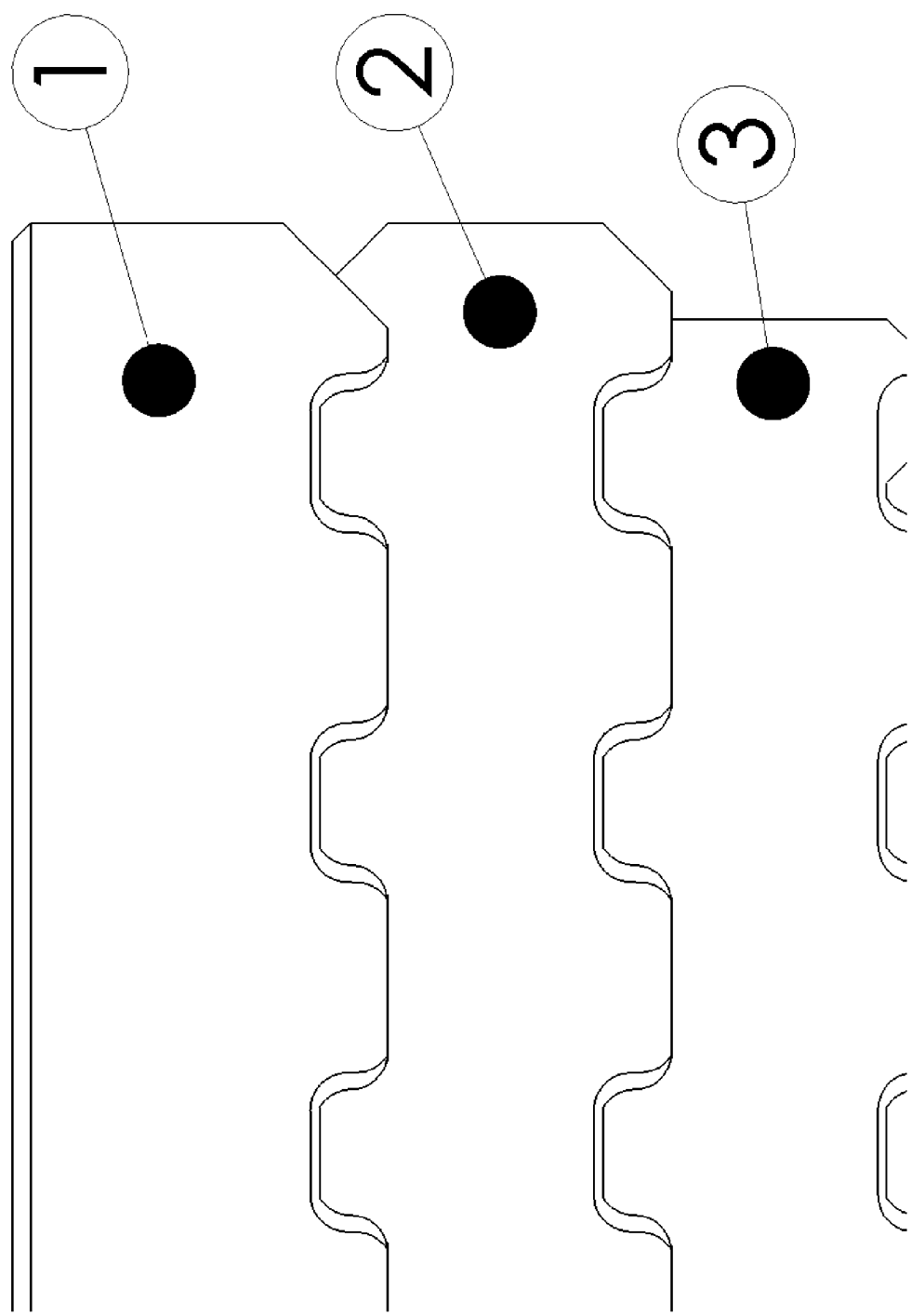
FIG. 6 is a side view of a tibial tray portion (1) with two stacked augment block portions (2 and 3).
Figure 7:
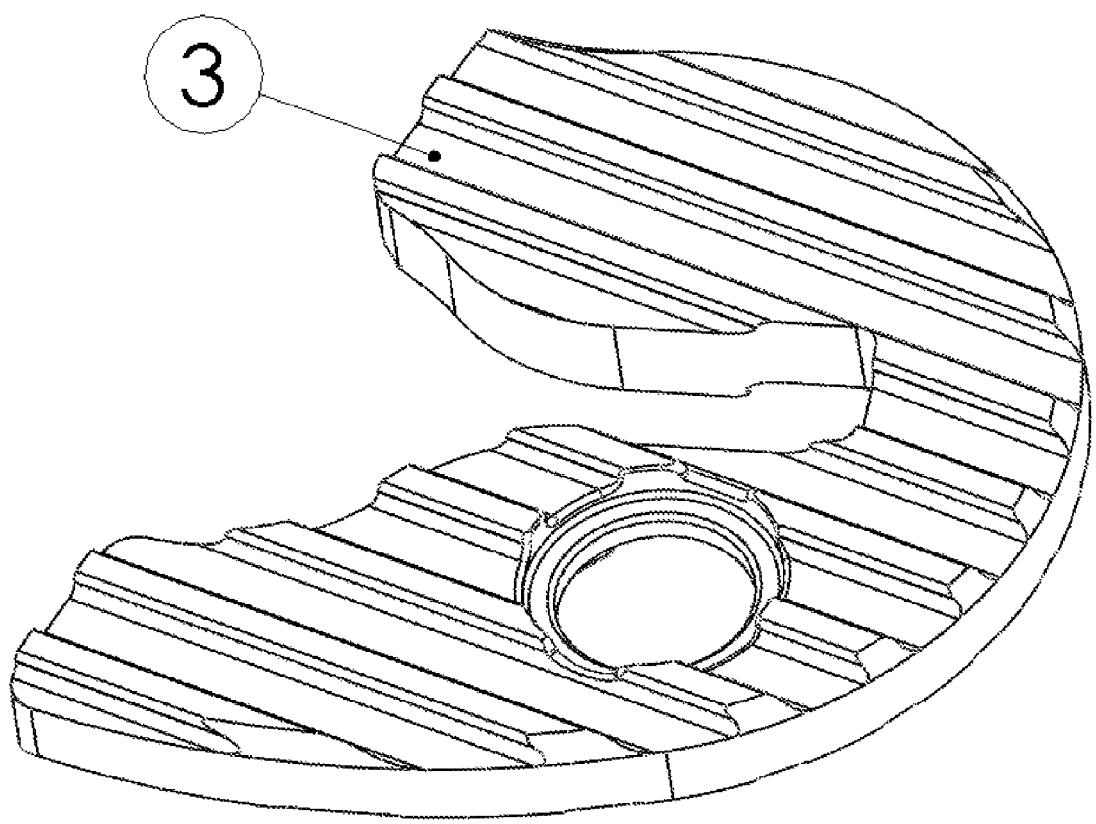
FIG. 7 is an augment block portion (3) with a through hole for the augment locking bolt portion and a cut-out area for clearance of a keel of a stem portion.

The augment block portions include geometric features forming relief patterns on the horizontal (proximal and distal) faces that create a mechanical interlock with opposing relief patterns on the underside of the tibial tray portion (FIGS. 3 and 7). The relief patterns are typically formed by ridges and grooves arranged in the desired pattern. The same features also interlock with the opposite face of another augment block portion (FIG. 6); the interlocking features on the opposite faces of the augment block portions are geometrically reversed (mirrored) to provide a mechanical interlock between adjacent stacked augment blocks (FIG. 6). Put another way, the interlocking features (in the case of FIG. 6, alternating ridges and grooves) form relief patterns on the surfaces of the augment blocks, such that a first relief pattern on one side of the augment block is complementary to a second relief pattern on the opposite side of the augment block. This can be most clearly seen in FIG. 6, where the ridges and grooves on the top of augment block 2 are aligned with, i.e., overlie, grooves and ridges respectively on the underside of the augment block 2. The result is that the relief pattern on the top of one augment block is complementary to and mates with the relief pattern on the underside of an identical augment block, or a relief pattern on the underside of the tray, so that stacked augment blocks can seat fully against and in register with one another and/or with the tray.

Although each ridge in the first, or medial, relief pattern has a corresponding, complementary groove in the second, or lateral relief, pattern, each ridge is typically not exactly the same size as its corresponding groove. Instead, each ridge is typically slightly narrower and shallower than its corresponding complementary groove, as shown in FIG. 6. Such approximately inverse relief patterns ease assembly without allowing for substantial play between complementary parts. Ridge edges may also be beveled, chamfered, rounded, or otherwise blunted to ease assembly.

Figure 8:
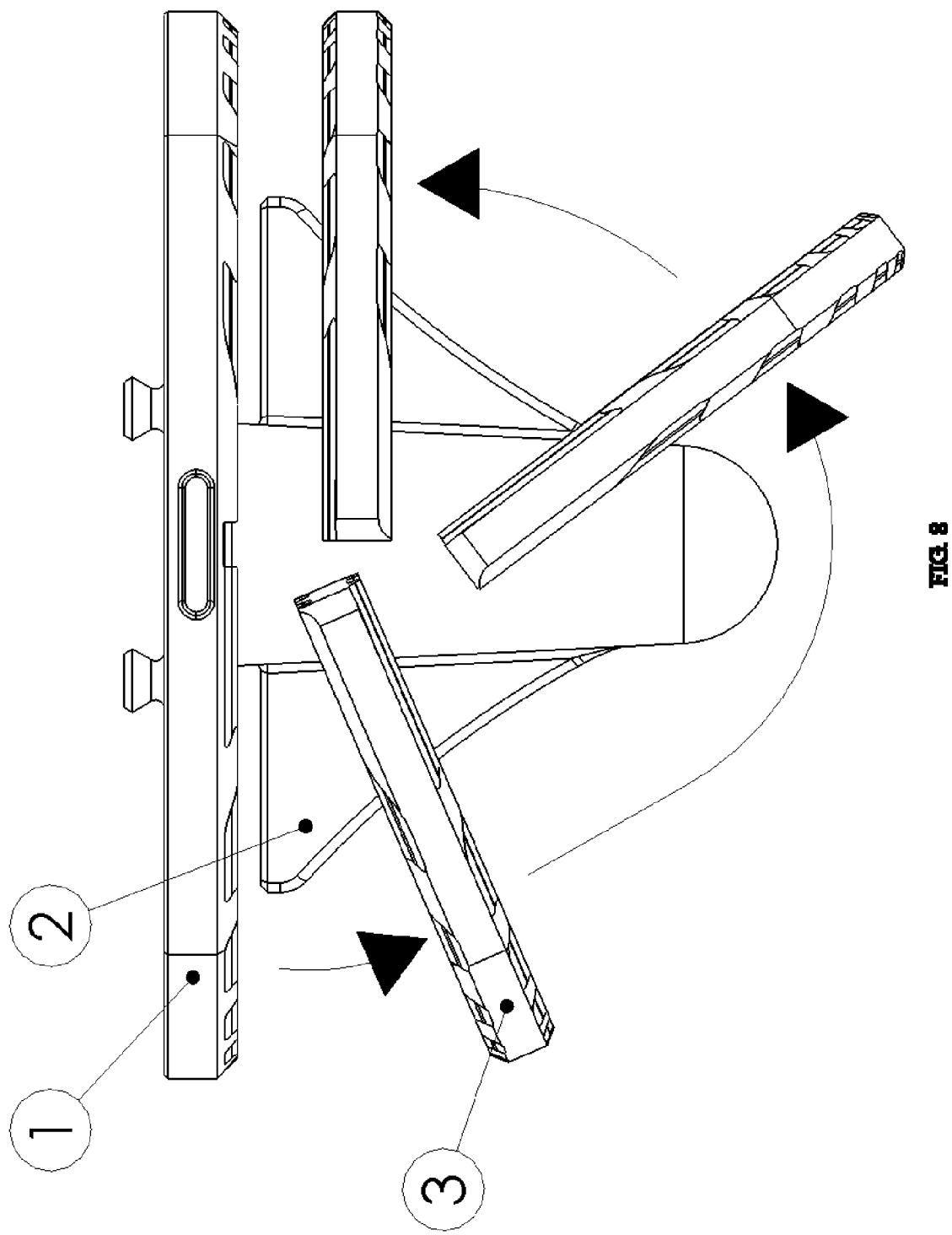
FIG. 8 is a graphical demonstration of the ability to flip an augment block portion (3) from one side of the tibial tray portion (1) to the other side of the tibial tray portion prior to insertion of an augment locking bolt portion.
Figure 11:
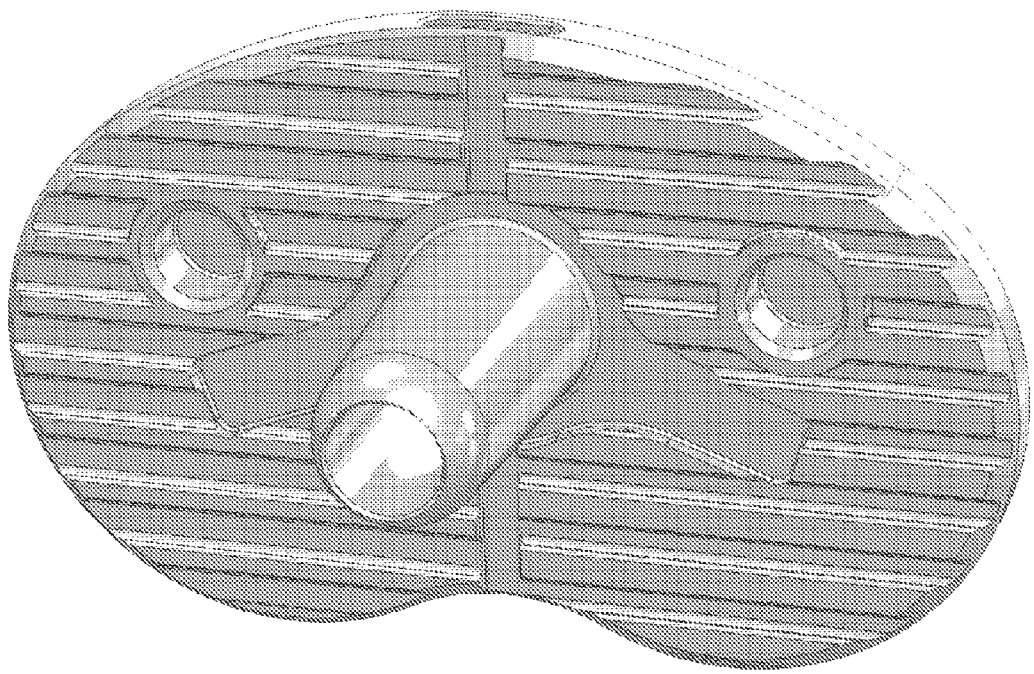
FIG. 11 is a distal view of the tibial tray portion of the prosthetic device.

The mating interlocking features on the underside of the tibial tray portion are likewise geometrically reversed between the medial and lateral sides of the tray (FIG. 11). The relief pattern on the medial underside of the tibial tray is complementary to, or roughly the inverse of, the relief pattern on the lateral underside of the tibial tray, as shown in FIG. 11 where grooves and ridges on the left side of the tray line up with ridges and grooves respectively on the right side of the tray. That is, if the medial relief portion were reproduced on a surface of an augment block, that augment block surface would seat fully against and in register with the lateral relief portion of the underside of the tray. In this way each side of the tibial tray portion is geometrically compatible, or complementary, with the same augment block portion by simply flipping the augment block portion to one side or the other prior to placement of the augment block locking bolt (FIG. 8); in either orientation, a mechanical interlock between the underside of the tibial tray portion and the proximal face of the augment block portion is created (FIG. 6). Put another way, the relief pattern on the underside of the lateral portion of the tibial tray would be complementary to a surface of an augment block, if that augment block's surface included the relief pattern. Fewer distinct parts need to be kept in inventory than if augment blocks could not simply be flipped to the required medial or lateral orientation.

Each portion of the underside of the tibial tray may be substantially covered by a relief pattern, or may have some areas free of relief. The surfaces of the augment block may likewise be substantially covered with the relief pattern. The ridges and grooves that form the relief pattern may be linear, as shown in, e.g., FIGS. 4, 7, 10 and 11. The linear ridges and grooves may run in any direction. The relief pattern may include other patterns as well, as long as the opposing relief patterns are complementary such that a pair of identical augment blocks, or an augment block and the tibial tray can seat fully on and in register with one another. For example, the ridges and grooves could be sinusoidal, or sawtooth-shaped, rather than linear, or they could form concentric polygons, circles, ellipses, or other curves. In fact, the pattern need not be regular at all, as long as the opposing relief patterns are complimentary. Ridges in a single relief pattern need not be the same size as each other, and need not be evenly spaced, as long as each ridge is complementary with a corresponding groove.

Figure 12:
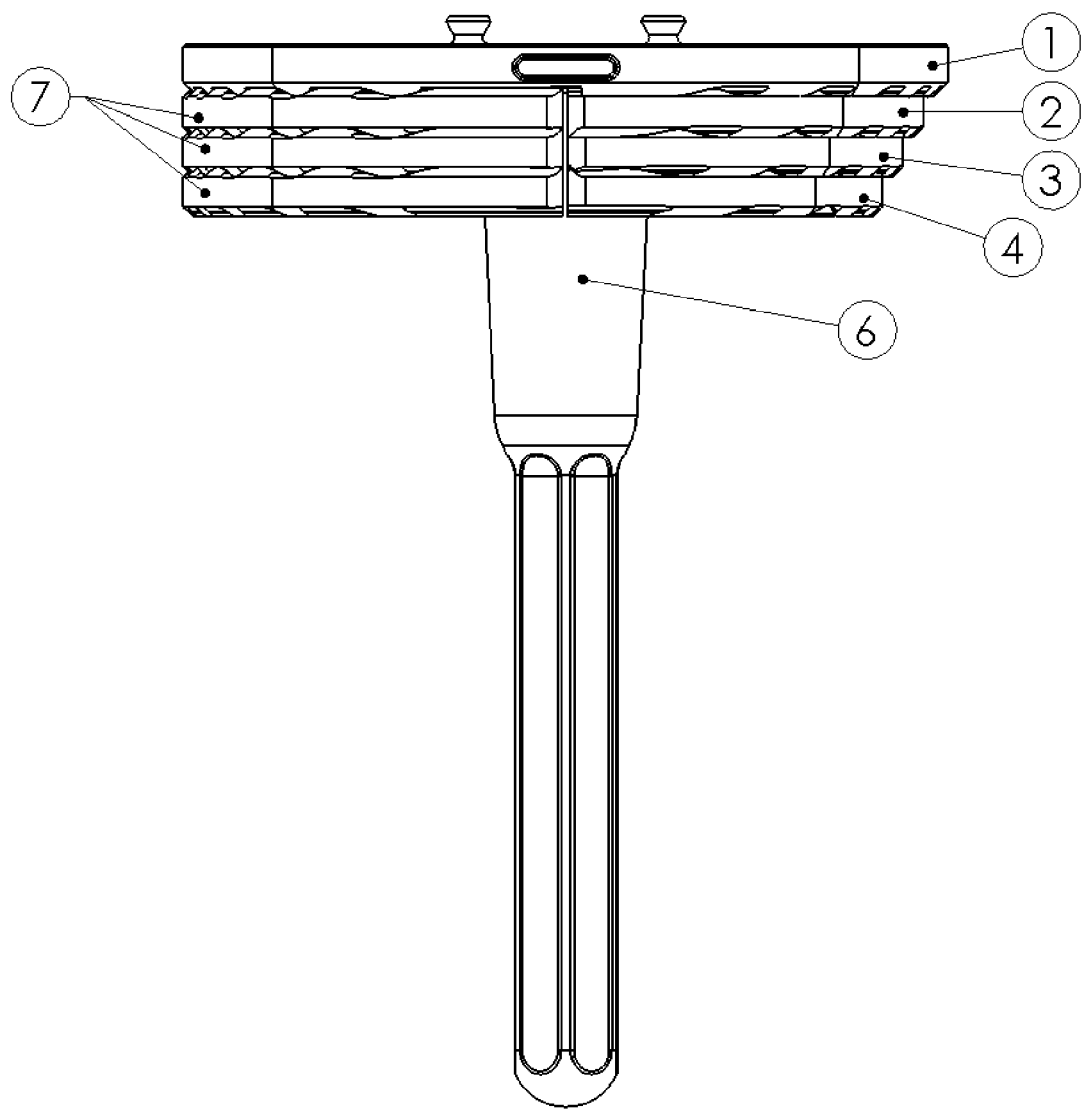
FIG. 12 is an anterior view of one embodiment of the assembled prosthetic device.

The augment block portions can be stacked independent of augment block portion size and thickness. For all augment blocks, the interlocking features are spatially compatible and the through holes for the augment block locking bolt (5) are in axial alignment (FIG. 7). In use, typical augment block stacks may be of a uniform size matching the tibial tray portion size, or may be of tapering size, with the most proximal augment block matching the size of the tibial tray portion, and with decreasing size augment block portions as the stack progresses distally, forming a distally tapering stack of augment block portions (FIG. 3 and FIG. 12). With one or more larger augment blocks on one side and one or more smaller augment blocks on the other side, the geometric center of the distal end of the augment blocks can be horizontally offset from the geometric center of the tibial tray (FIG. 12). A tapered stack of augment blocks may or may not take advantage of the mating relief patterns described above.

For augment blocks and/or the tray to be in register, it need not be the case that the outer edges are perfectly aligned. For example, the stacked augment blocks 2-4 shown in FIGS. 3 and 12 are in register even though the augment blocks form a tapered stack in which none of the outer edges align with one another. In this case, the augment blocks are in register because they define through holes, each of which has an axis, with all the axes aligned. This allows a single augment block locking bolt 5 to pass through the aligned through holes. The tray likewise defines a bore, possibly a blind hole or a through hole, that has its own bore axis. The bore axis is aligned with the through-hole axes so that the augment block locking bolt 5 can enter the bore as well.

Figure 5:
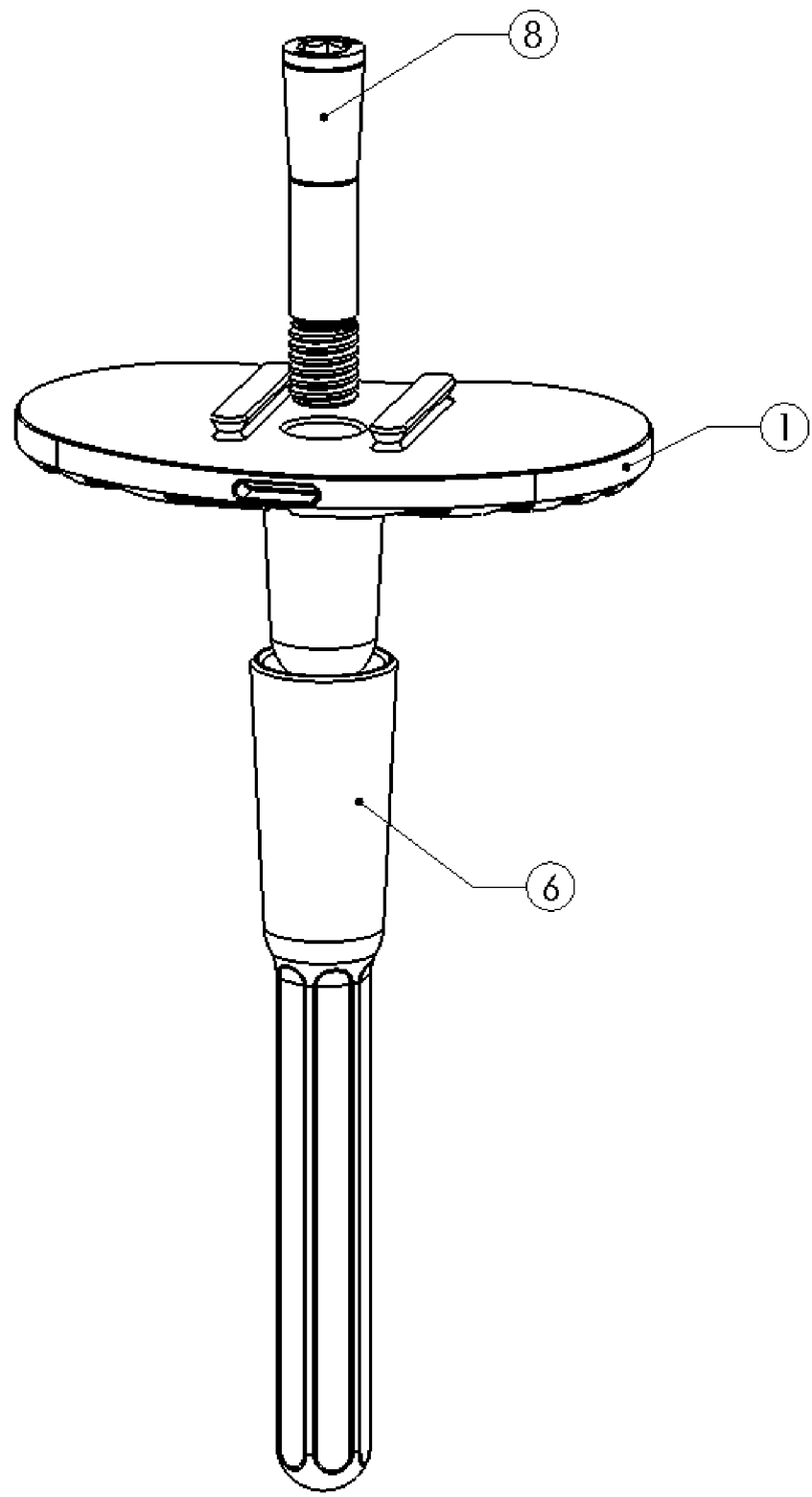
FIG. 5 is an exploded distal view of one embodiment of the prosthetic device.

The stem portion (6) is attached to the tray portion (1) with a stem locking bolt portion (8) and a tapered engagement between the outer surface of the distal extension of the tray portion and the inner surface of the proximal stem (FIG. 5). The stem locking bolt portion passes through the tibial tray portion, including the distal extension, and engages the stem portion using threads or other structure. The head of the stem locking bolt portion engages the central hole in the tray portion. In the preferred embodiment, the head of the stem locking bolt has an external taper that is compatible with an internal taper on the central through hole in the tibial tray portion.

The stem portion can be straight, tapered, curved, or other shapes as appropriate to fit within the prepared tibial canal. The stem can have a surface and shape that is appropriate for use with bone cement, such as the hexagonal flat-sided distal geometry (FIG. 5). The stem can optionally have a coating, porous architecture, or otherwise be prepared or treated for fixation to the adjacent bone without use of bone cement.

Figure 9:
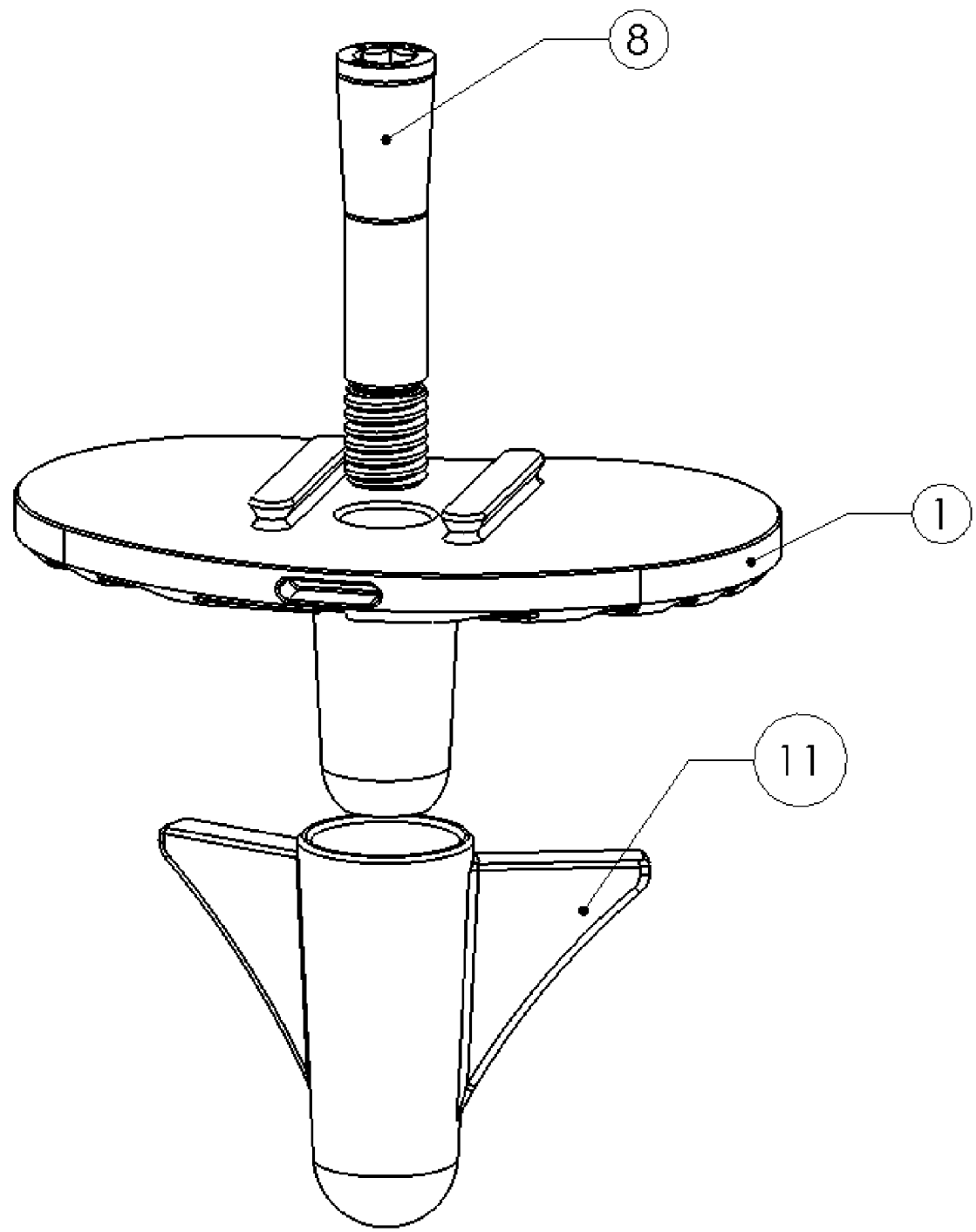
FIG. 9 is an exploded distal view of one embodiment of the prosthetic device.
Figure 10:
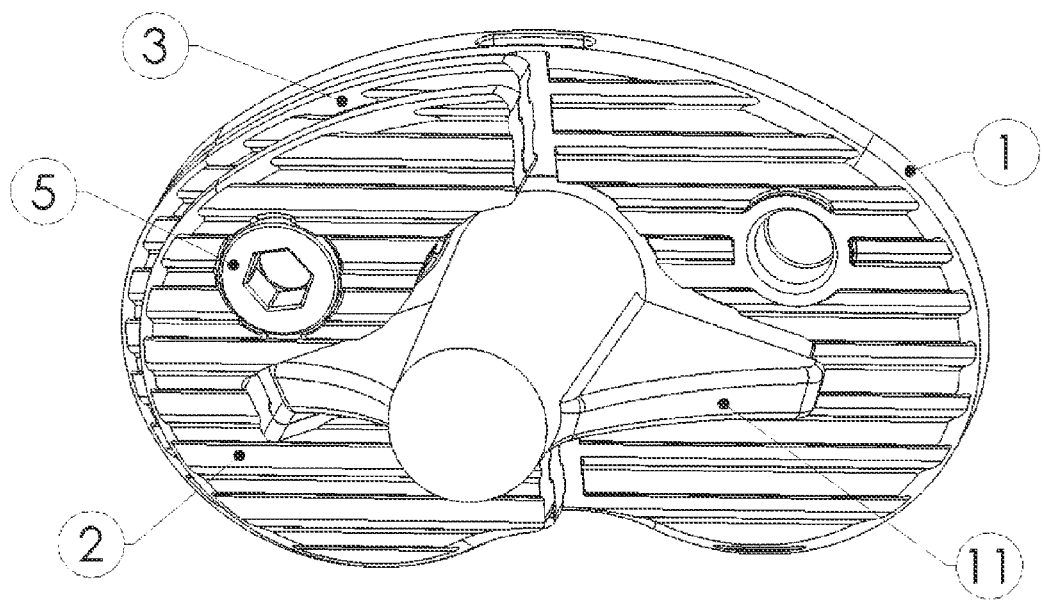
FIG. 10 is a distal view of one embodiment of the prosthetic device.

In another embodiment, the stem can have one or more keels (11) that can provide additional rotational stability to the tibial tray construct (FIGS. 9 and 10). The augment block portions may include a slot that fits around a keel (11) allowing one or more augment block portions to be used with a stem with one or more keels (FIGS. 7 and 10).

Figure 13:
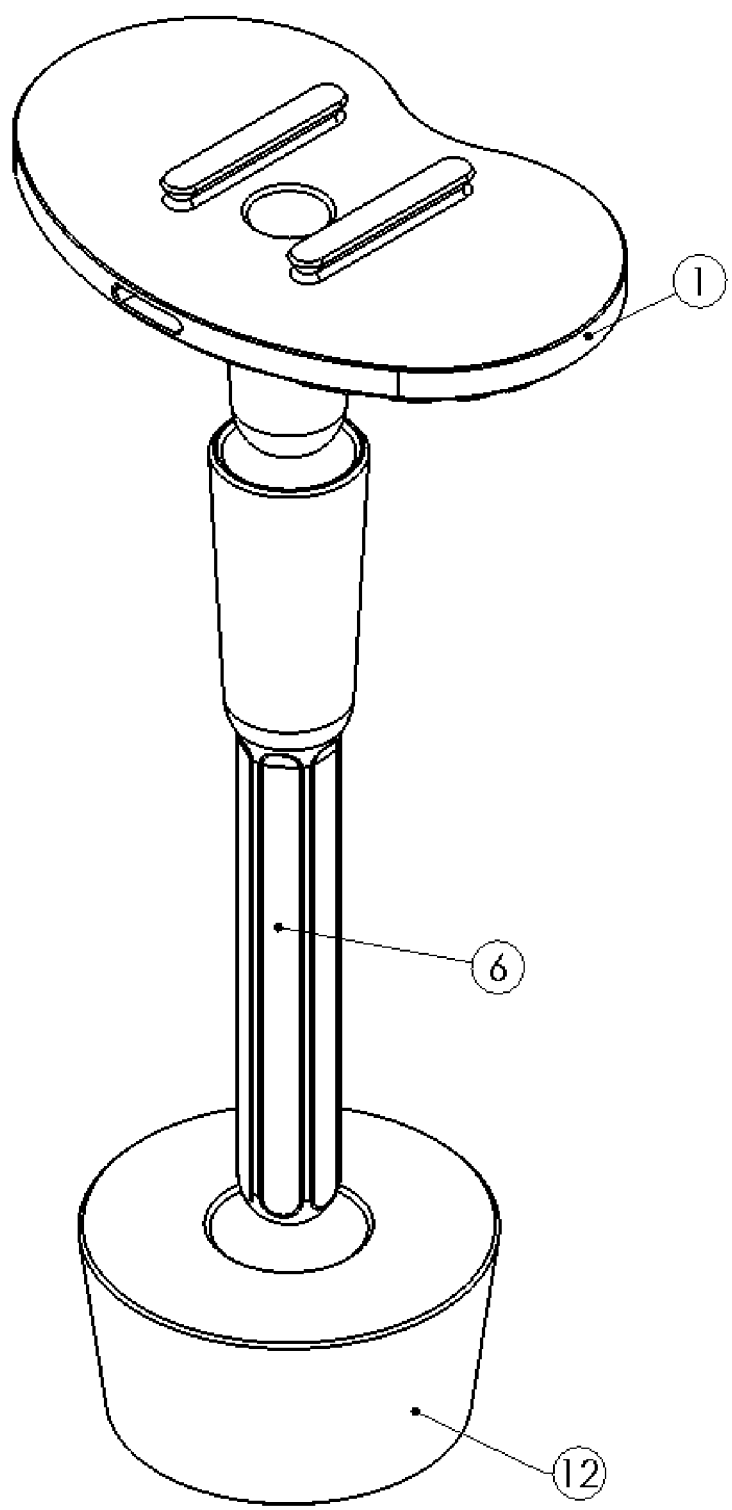
FIG. 13 is an exploded distal view of one embodiment of the prosthetic device.
Figure 14:
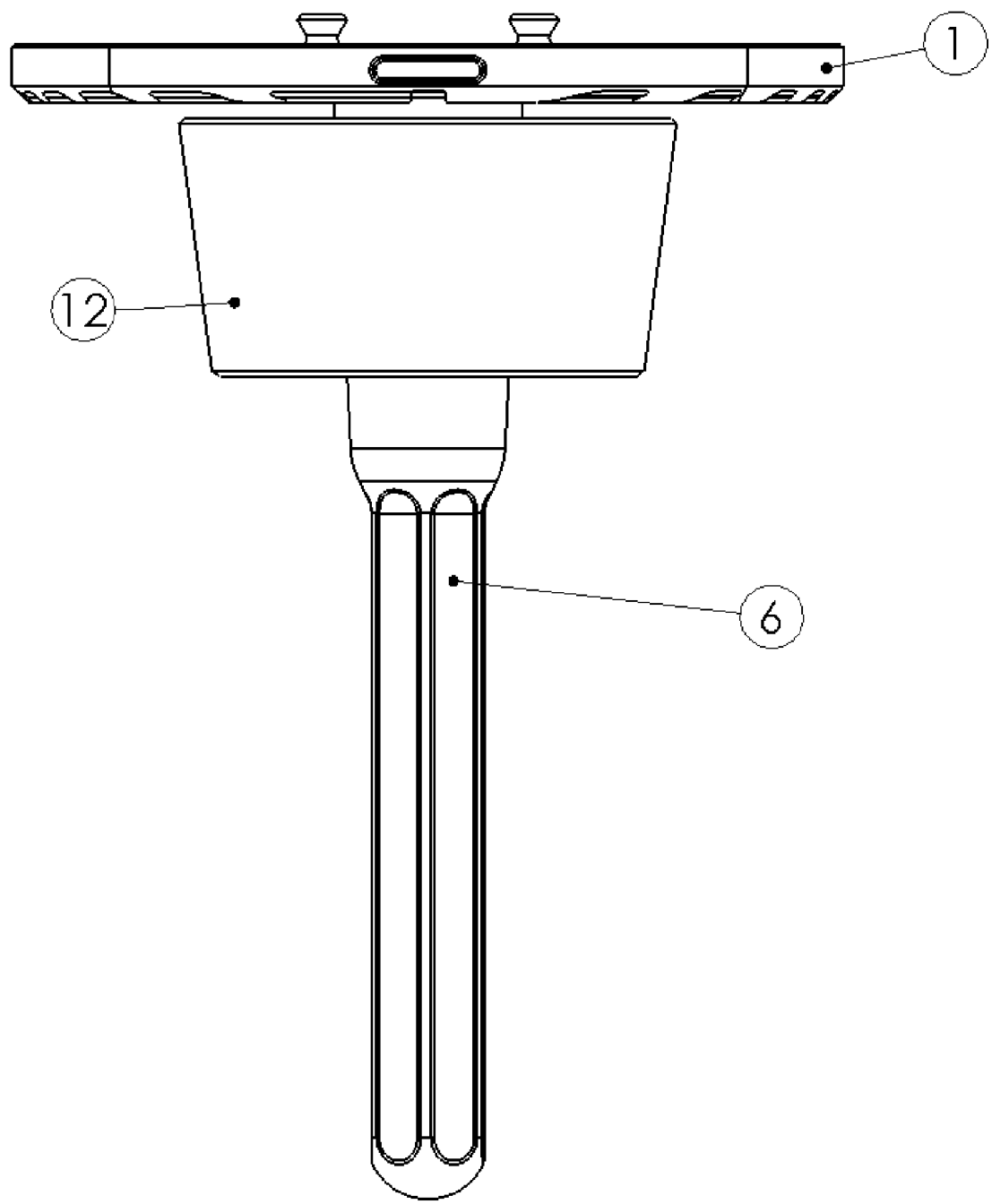
FIG. 14 is an anterior view of one embodiment of the prosthetic device.

In another embodiment, the proximal end of the stem portion (6) includes an external tapered region that optionally can be used to attach other portions to the stem, such as a cone-shaped bone filling augment (12, FIG. 13 and FIG. 14). This bone filling augment can optionally have external features, coating, porous architecture, or otherwise be prepared or treated for fixation to the adjacent bone without use of bone cement.

Figure 15:
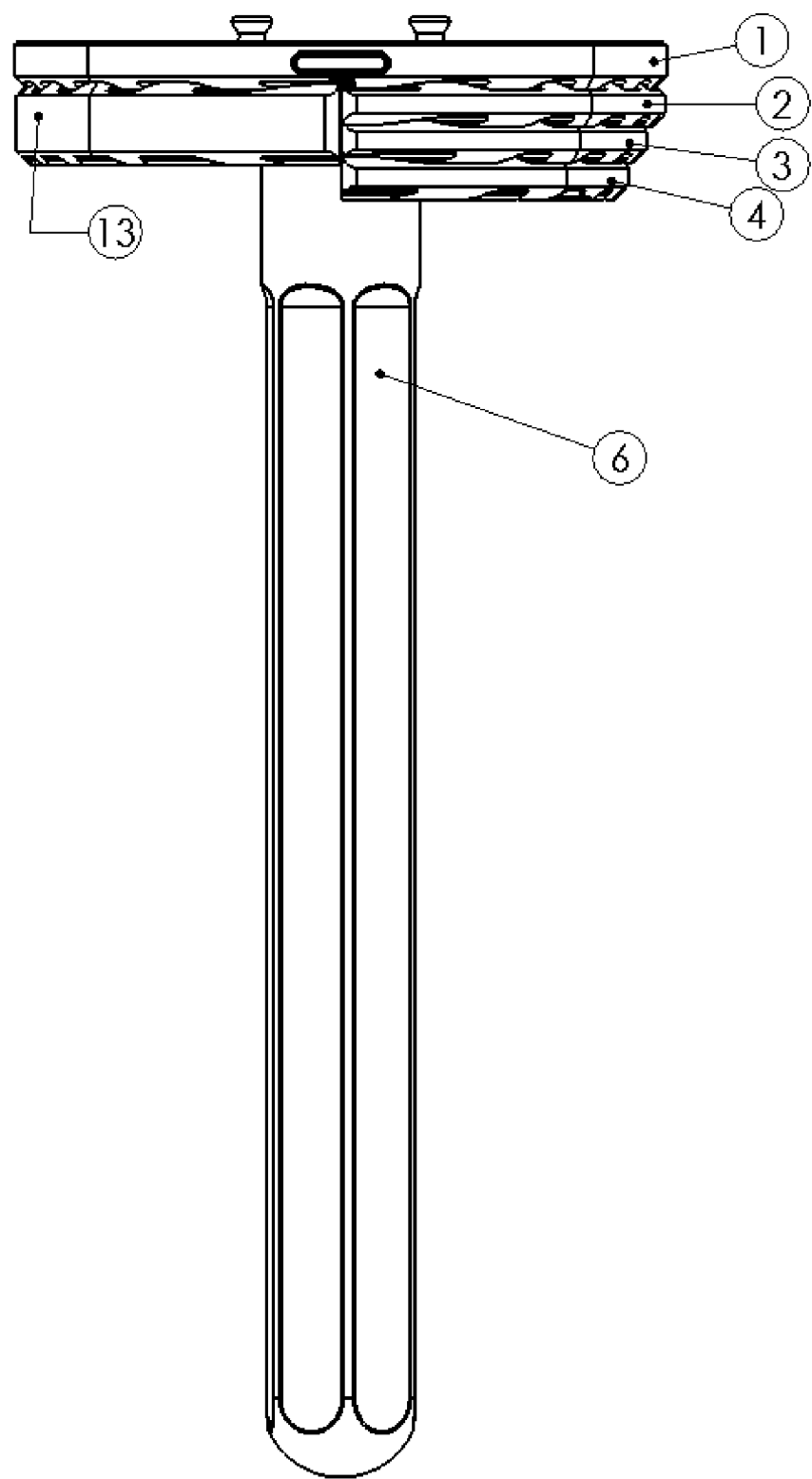
FIGS. 15-16 show alternative embodiments of modular tibial knee prostheses.
Figure 16:
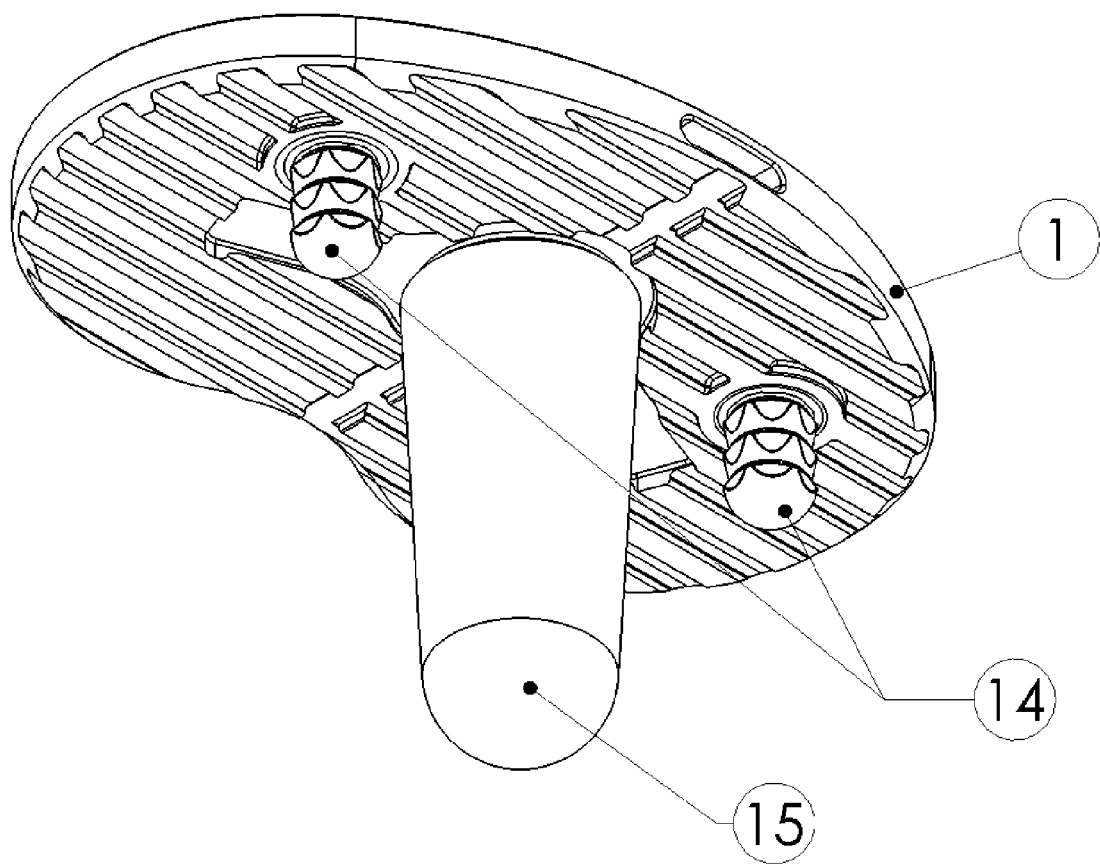

FIG. 15 shows an embodiment having augment blocks of different thicknesses. Also shown in FIG. 15 is a stem having a larger diameter than shown in other drawings. FIG. 16 shows an embodiment with modular pegs (14) threaded into the holes, in place of the augment locking bolt (augment blocks are omitted for clarity). FIG. 16 also shows a tapered stem (15) with a rounded distal tip.

The assembly of the device is not limited temporally, in that assembly can occur before surgery, immediately prior to implantation, or during implantation. The device components can, for example, be assembled from a kit that includes a tray, one or more augment blocks, a first articulating member and a second articulating member. The articulating members can be sized and shaped to articulate with each other so as to model flexion in the replaced joint. The first articulating member can be affixed to the top of the tray, while the underside of the tray has lateral and medial relief patterns as described above. The augment blocks have opposed first and second surfaces having the same relief patterns as the medial and lateral portions of the underside of the tray, also as explained above. Multiple augment blocks may be used as shown in FIG. 7. The augment blocks 7 could all be the same size, so that they can form a stack of constant, i.e., non-tapering, width. Alternatively, the augment blocks need not all be the same size. Any combination of variously sized augment blocks might be useful, depending on the anatomy being modeled. In particular, the augment blocks 2-4 might all be different sizes, so that when stacked the blocks form a tapered structure.

The tibial tray (1), augment portions (2-4, 7, and 12), stem portion (6, 11), augment locking bolt portion (5), and stem locking bolt portion (8) of this device can be fabricated from any suitable high strength biocompatible material. Suitable materials include any of the titanium alloys, cobalt alloys, or stainless steel alloys. Preferred examples include Ti-6Al-4V or cobalt chrome alloy for the tibial tray, stem, augment block, and locking bolt portions.

We claim:

1. A tray for a joint prosthesis, the tray comprising a superior surface and an inferior surface, the inferior surface comprising a medial portion and a lateral portion, wherein:
    the medial portion comprises ridges and grooves arranged in a medial relief pattern;
    the lateral portion comprises ridges and grooves arranged in a lateral relief pattern; and
    wherein a longitudinal axis of the ridges of the medial portion align with a longitudinal axis of the grooves of the lateral portion.

2. The tray of claim 1, wherein the medial relief pattern covers substantially all of the medial portion of the inferior surface, and the lateral relief pattern covers substantially all of the lateral portion of the inferior surface.

3. The tray of claim 1, wherein the ridges and grooves of the medial relief pattern are linear.

4. The tray of claim 1, further comprising an augment block comprising ridges and grooves arranged in the medial relief pattern for seating against and in registering with the lateral portion of the tray entirely within the inferior surface of the lateral portion.

5. The tray of claim 4, wherein each ridge on the lateral portion is narrower than a corresponding groove of the medial relief pattern so as to avoid an interference fit when the augment block is fully seated against and in register with the lateral portion.

6. The tray of claim 1, wherein the ridges on the medial portion of the inferior surface have a width different from a width of the ridges on the lateral portion of the inferior surface.

7. The tray of claim 1, wherein the ridges on the medial portion of the inferior surface have a height different from a height of the ridges on the lateral portion of the inferior surface.

8. The tray of claim 1, wherein an entirety of the ridges and grooves of the medial relief pattern would be capable of fully seating within the inferior surface of the tray.

9. A tray for a joint prosthesis comprising: a superior surface; and an inferior surface that includes: a lateral portion having ridges and grooves arranged in a lateral relief pattern, and a medial portion having ridges and grooves arranged in a medial relief pattern, wherein the medial relief pattern is an interlocking relief pattern of the lateral relief pattern, and wherein the medial relief pattern and lateral relief pattern each extends completely to an outer circumferential end of the inferior surface.

10. The tray of claim 9, wherein the medial relief pattern covers substantially all of the medial portion of the inferior surface, and the lateral relief pattern covers substantially all of the lateral portion of the inferior surface.

11. The tray of claim 9, wherein the ridges and grooves of the medial relief pattern are linear.

12. The tray of claim 9, wherein the ridges on the medial portion of the inferior surface have a width different from a width of the ridges on the lateral portion of the inferior surface.

13. The tray of claim 9, wherein the ridges on the medial portion of the inferior surface have a height different from a height of the ridges on the lateral portion of the inferior surface.

14. The tray of claim 9, wherein an entirety of the ridges and grooves of the medial portion is capable of seating within the inferior surface of the tray.

15. A tray for a joint prosthesis comprising:
    a superior surface;
    an inferior surface that includes:
        a lateral portion having ridges and grooves arranged in a lateral relief pattern, and
        a medial portion having ridges and grooves arranged in a medial relief pattern that is complementary to the lateral relief pattern; and
    an augment block attachable to the inferior surface, the augment block having ridges and grooves configured the same as the ridges and grooves on the inferior surface, wherein a longitudinal axis of a ridge and a groove on the augment block both align with one of a ridge or a groove of the inferior surface in a single plane when attached to the inferior surface.

16. The tray of claim 15, wherein the medial relief pattern covers substantially all of the medial portion of the inferior surface, and the lateral relief pattern covers substantially all of the lateral portion of the inferior surface.

17. The tray of claim 15, wherein the ridges and grooves of the medial relief pattern are linear.

18. The tray of claim 15, wherein ridges on the inferior surface overlie grooves on a first surface of the augment block.

19. The tray of claim 15, wherein each ridge on the inferior surface is narrower than a corresponding groove of the augment block so as to avoid an interference fit.

20. The tray of claim 15, wherein the ridges on the medial portion of the inferior surface have a width different from a width of the ridges on the lateral portion of the inferior surface.

21. The tray of claim 15, wherein the ridges on the medial portion of the inferior surface have a height different from a height of the ridges on the lateral portion of the inferior surface.

22. The tray of claim 15, wherein the augment block further includes a first and a second surface, wherein the first surface of the augment block is configured with one of the medial or lateral relief patterns and the second surface is configured with the other of the medial or lateral relief patterns.

* * * * *